United States Patent [19]

Mueller et al.

[11] 4,189,591

[45] Feb. 19, 1980

[54] METHOD OF PREPARING 4-METHYL-5-HYDROXYMETHYL-IMIDAZOLE

[75] Inventors: Hans-Rudolf Müeller; Werner Küendig, both of Schaffhausen; Alfred Hedinger, Thayngen, all of Switzerland

[73] Assignee: Eprova Aktiengesellschaft, Schaffhausen, Switzerland

[21] Appl. No.: 6,533

[22] Filed: Jan. 25, 1979

[30] Foreign Application Priority Data

Apr. 7, 1978 [CH] Switzerland .......................... 3755/78

[51] Int. Cl.$^2$ .......................................... C07D 233/64
[52] U.S. Cl. .................................................. 548/342
[58] Field of Search ........................................ 548/342

[56] References Cited

U.S. PATENT DOCUMENTS 4,104,473  8/1978  Sawa et al. ............................ 548/342

OTHER PUBLICATIONS

Godefroi et al., Recueil des travaux chimiques de pays/-bas 1972, vol. 91, pp. 1383–1392.
Grindley et al., J. Chem. Soc. (London) 1927, pp. 3128–3136.
Hofmann, Imidazole and Its Derivatives Part I, pp. 99–100, N.Y., Interscience, 1953.
Masui et al., Chem. Pharm. Bull. 1974, vol. 22, pp. 2359–2364.
Windaus Berichte (Deutsche Chem. Gesellschaft) 1909, vol. 42, pp. 758–763.

*Primary Examiner*—Natalie Trousof
*Attorney, Agent, or Firm*—Toren, McGeady and Stanger

[57] ABSTRACT

The yield of 4-methyl-5-hydroxymethyl-imidazole from the known reaction between formaldehyde and 4-methyl-imidazole can be increased greatly if the reaction is performed in a concentrated aqueous medium at pH 11–13.5, preferably 12–13.5, at a temperature of 20°–60° C., preferably 30°–40° C., with an amount of formaldehyde not exceeding 1.5 mole per mole of 4-methylimidazole.

4 Claims, No Drawings

METHOD OF PREPARING 4-METHYL-5-HYDROXYMETHYL-IMIDAZOLE

This invention relates to the preparation of 4-methyl-5-hydroxymethyl-imidazole, and particularly to the preparation of the compound by hydroxy-methylation of 4-methyl-imidazole by means of formaldehyde.

4-Methyl-5-hydroxymethyl-imidazole has been a known intermediate in the preparation of pharmaceutical and other compounds for many years. It recently became an important starting material for the preparation of cimetidine.

The formation of small amounts of 4-methyl-5-hydroxymethyl-imidazole by the reaction of formaldehyde with 4-methyl-imidazole was discovered by Windaus in 1909, and others were able to improve the yield to approximately 40% (R. Grindley et al., J. Chem. Soc. 1929, 3128), based on the 4-methyl-imidazole employed as a starting material. Because of the low yield and the difficulty of recovering a product of adequate purity from the reaction mixture, the production of 4-methyl-5-hydroxymethyl-imidazole on an industrial scale was based heretofore on the electrochemical reduction of imidazole-carboxylix acids and their esters (see Brit. Pat. No. 1,341,376 and German Patent Publication 2,538,621), a relatively costly procedure often requiring costly starting materials.

It has now been found that the yield of the known reaction between formaldehyde and 4-methyl-imidazole can be more than doubled over the best results achieved heretofore by carrying out the reaction under closely controlled conditions, combining an alkaline reaction medium having a pH value of 11 to approximately, and preferably 12–13.5, a reaction temperature between 20° and 60° C., optimally 30°–40° C., and an amount of formaldehyde not greater than 1.5 moles per mole of 4-methyl-imidazole.

A large excess of formaldehyde in the reaction mixture is avoided most conveniently by gradually adding the formaldehyde during the course of the reaction at approximately the same rate at which it is consumed.

The reaction is carried out best in an aqueous medium, and a high concentration of the reactants is beneficial. The necessary pH value is preferably established and/or maintained by addition of sodium hydroxide, but other alkali metal hydroxides and alkali metal salts of weak acids, such as the carbonates or sulfites may be used as alkalinizing agents. Formaldehyde is most economically added to the reaction mixture in the form of its commercially available concentrated solutions, but homopolymers of formaldehyde, such as paraformaldehyde may be employed.

When the reaction mixture is neutralized after completion of the reaction, and water is removed by evaporation and by azeotropic distillation with a lower alkanol (isopropanol, isobutanol, 2-butanol), the free base may be crystallized from the alcoholic solution. Crystallization is assisted by the addition of acetone or another non-solvent miscible with the alcohol present.

The crystals so obtained are 98 to 99% pure, and no significant amount of by-products can be found in a thin-layer chromatogram. An additional amount of 4-methyl-5-hydroxymethyl-imidazole can be recovered from the mother liquor in the form of an addition salt of the base with an organic or inorganic acid, such as hydrochloride or the 2-(4-chlorobenzoyl)-benzoate. A total recovery of 80–90% of the original 4-methyl-imidazole in the form of 4-methyl-5-hydroxymethyl-imidazole and its salts is readily achieved. If so desired, the entire 4-methyl-5-hydroxymethyl-imidazole present in the reaction mixture may be recovered in the form of an addition salt.

The product is colorless if the formaldehyde is reacted in the alkaline reaction medium under a protective, non-oxidizing atmosphere, such as nitrogen or argon. The cost of a product suitable for pharmaceutical use prepared by the method of the invention is sharply lower than that of any method available heretofore.

The advantages of this invention are available only from a combination of the reaction conditions enumerated above. At room temperature and a pH of less than 11, no significant amounts of 4-methyl-5-hydroxymethyl-imidazole can be found in the reaction mixture. At pH 10.4–10.5 and 30° C., 100% of the original 4-methyl-imidazole is found unreacted after 65 hours regardless of the amount of formaldehyde present. The reaction rate rises steeply with increasing pH.

At room temperature (about 20° C.) and pH 11.5, about 50% of the 4-methyl-imidazole is consumed after 75–100 hours. When a reaction mixture was held at pH 11.6 and room temperature for 72 hours, 59% of the 4-methyl-imidazole could be recovered as 4-methyl-5-hydroxymethyl-imidazole.

At a temperature of 30° C. and pH 11.5, one half of the 4-methyl-imidazole originally present was consumed in 45 hours. 70% 4-Methyl-imidazole was converted to 4-methyl-5-hydroxymethyl-imidazole at pH 12.7–12.8 at 30° C. within 10 hours, and the conversion reached 97% after 26 hours. Conversion rates exceeding 80% were achieved at pH 12.3–12.8 after 65–75 hours at ambient temperature, and the pH value of the reaction mixture rose spontaneously to 13.0–13.4 during the late stages of the reaction. The necessary reaction time is reduced by moderately raising the temperature. The following Table indicates the conversion rates (in percent) observed during reaction of 4-methyl-imidazole with equimolecular amounts of formaldehyde at 12.7 at varying temperatures after different times:

TABLE

| Temp., °C. | 1 | 2 | 3 | 4 | 5 | 6 | 8 | 11 | 12 | 21 | 23 |
|---|---|---|---|---|---|---|---|---|---|---|---|
| 30 | | | | 36 | | | 53 | | 67 | | 90 | |
| 40 | | | 43 | | 75 | | | 85 | | 90 | | 95 |
| 50 | 59 | 75 | 83 | | 95 | | | | | | | |

The best recovered yields achieved from reaction mixtures obtained at the several temperatues listed were 79–84% at 30° C., 93% at 40° C., but only 80% at 50° C. which yielded a somewhat discolored product. The color further deteriorates and the recovered yield decreases as the temperature is raised beyond 50°, and particularly beyond 60° C.

Erlenmeyer et al. [Helv. Chim. Acta 31 (1948) 38] reported yields of 53% to 59% from a reaction of one mole 4-methyl-imidazole with 2.75 moles formaldehyde when pH and temperature were optimally selected. We have found that yields in excess of 80% are achieved under otherwise unchanged conditions when the amount of formaldehyde is reduced to 1–1.2 moles.

Best yields are achieved in a short time in aqueous reaction media containing the reactants at high concentration. When the water is replaced by methanol, only trace amounts of 4-methyl-5-hydroxymethyl-imidazole can be found in the reaction mixture. The other common solvents are no better, and water is cheaper than any other solvent that would be operative.

The following Examples are further illustrative of this invention:

EXAMPLE 1

164.2 g of 4-Methyl-imidazole (2 mole) was melted, 36 g (2 mole) water was added, and the mixture was stirred under a nitrogen atmosphere until a solution was obtained. 166.4 g Aqueous 36.1% formaldehyde solution (2.0 mole) was added dropwise with stirring and external cooling at such a rate that the temperature did not substantially exceed 30° C. The reaction mixture then was adjusted to pH 12.4 with 20 ml sodium hydroxide solution containing 40 g NaOH per 100 ml, and stirring was continued at 30° C. for 24 hours while the pH was held between 12.2 and 12.4 by further additions of sodium hydroxide solution.

Thereafter, 16.6 g formaldehyde solution (0.2 mole) was added, the mixture was adjusted to 12.5 and further stirred for 48 hours. After approximately four hours, 0.39 mole NaOH had been added to maintain a pH of at least 12.2, but the pH value thereafter rose spontaneously, reaching 12.9 after 24 hours, 13.1 after 45 hours, and 13.1 after 70 hours.

The reaction mixture then was neutralized by addition of concentrated hydrochloric acid and most of the water present was evaporated in a vacuum while the mixture was immersed in a water bath at 40° C. The residue weighing 350 g was dissolved in 900 ml 2-butanol. Additional water was removed by distilling off 500 ml 2-butanol. Sodium chloride that had precipitated from the mixture was removed by filtration under pressure at 40° C. 74 g Gaseous hydrogen chloride was introduced into the clear filtrate which was held under a nitrogen blanket and cooled to a temperature of not more than 40° C., whereby the hydrochloride of 4-methyl-5-hydroxymethyl-imidazole started crystallizing. The crystal crop was increased by partial evaporation of the mother liquor and addition of acetone, and 238 g 4-methyl-5-hydroxymethyl-imidazole hydrochloride (80% of theoretical yield based on the 4-methylimidazole used) was recovered by filtration with suction. It melted at about 240° C. (decomp.) and was found to contain 100.8% of the theoretically expected amount of the base.

EXAMPLE 2

2 Mole 4-methyl-imidazole was reacted with the formaldehyde solution referred to in the preceding Example at pH 12-13 at 40° C. The reaction was completed after only 50 hours. The reaction solution was neutralized with hydrochloric acid, evaporated to dryness in a vacuum, mixed with isopropanol, further dehydrated by azeotropic distillation of the alcohol, and separated from precipitated sodium chloride by pressure filtration. The clear filtrate was further evaporated, and the concentrate was mixed with acetone. 4-Methyl-5-hydroxymethyl-imidazole crystallized and was recovered by filtration with suction in an amount of 153 g (68% yield). It melted at 136° C.

41 g 4-Methyl-5-hydroxymethyl-imidazole hydrochloride was recovered from the mother liquor by saturating the same with hydrogen chloride gas to increase the yield by 13.8%. When the mother liquor obtained in a second, identical run was mixed with 2-(4-chlorobenzoyl)-benzoic acid instead of the gaseous hydrogen chloride, 104 g crystalline 4-methyl-5-hydroxymethyl-imidazole salt of the benzoic acid derivative was recovered, corresponding to an additional yield of 13.9%. The salt melted at about 150° C. (decomp.) and its equivalent weight was found in two tests to be 375.0 and 373.0 respectively, as compared to a calculated value of 372.8.

EXAMPLE 3

A mixture of 164.2 g molten 4-methyl-imidazole and 36 g water was adjusted to pH 12.3 with aqueous sodium hydroxide solution, and 166.4 g 36.1% formaldehyde solution was added gradually to the reaction mixture over 24 hours while the temperature was kept at 30° C. and the pH value was maintained between 12.3 and 12.6 until it rose spontaneously and gradually to 13.3. Stirring at 30° C. was continued for 48 hours after the addition of formaldehyde was completed.

After the reaction solution was worked up as in Example 2, 176.7 g 4-methyl-5-hydroxymethyl-imidazole (78.8% yield) was recovered. Additional 9.8 g 4-methyl-5-hydroxymethyl-imidazole hydrochloride was crystallized from the mother liquor, making the total yield 82.1%.

EXAMPLE 4

164.2 g. Freshly distilled 4-methyl-imidazole (2 mole) was mixed with 54 g water (3 mole), and the mixture was warmed gently under a nitrogen blanket until a solution was obtained. It was adjusted to 20° C., and 66.1 g paraformaldehyde (2.2 mole) was added in small batches, followed by 10.4 g sodium hydroxide in several portions to raise the pH to 12.6. The reaction solution so obtained was stirred 20 hours at 40° C. and reached a pH of 13.1.

The resulting crystal slurry was mixed with 50 g isopropanol and, stirred at 40° C. maintained by external water cooling while 20.3 ml concentrated hydrochloric acid was added. The neutralized mixture was evaporated to dryness, and additional water was removed by addition and azeotropic distillation of isopropanol. The product was then dissolved in 250 ml isopropanol at 75° C., and the solution was filtered while hot to remove precipitated sodium chloride. The clear filtrate was partly evaporated and mixed with acetone in the manner described in Example 2 to induce crystallization of 4-methyl-5-hydroxymethyl-imidazole which was recovered in an amount of 190 g (84.7 yield).

The mother liquor was evaporated to dryness, the residue dissolved in hot isopropanol, and 58 g 4-methyl-5-hydroxymethyl-imidazole 2-(4-chlorobenzoyl)-benzoate was recovered as described in Example 2, to raise the yield to 92.5% of the theoretical yield based on the 4-methyl-imidazole employed as a starting material.

It should be understood, of course, that the foregoing disclosure relates only to preferred embodiments of the invention, and that it is intended to cover all changes and modifications of the examples chosen for the purpose of the disclosure which do not constitute departures from the spirit and scope of the invention set forth in the appended claims.

What is claimed is:

1. In a method of preparing 4-methyl-5-hydroxymethyl-imidazole by reaction of 4-methyl-imidazole with formaldehyde the improvement in the reaction conditions which comprises:
   (a) an alkaline reaction medium having a pH value between 11 and approximately 13;

(b) a reactiontemperature between 20° and 60° C.; and (c) an amount of said formaldehyde not greater than 1.5 moles per mole of said 4-methyl-imidazole.

2. In a method as set forth in claim 1, said formaldehyde being added gradually to said 4-methyl-imidazole during said reaction.

3. In a method as set forth in claim 1, said formaldehyde being added to said 4-methyl-imidazole in the form of a homopolymer thereof.

4. In a method as set forth in claim 1, said pH value being between 12 and 13.5, said reaction temperature between 30° and 40° C., and said medium being aqueous.

* * * * *